United States Patent [19]
Notari et al.

[11] Patent Number: 5,849,955
[45] Date of Patent: Dec. 15, 1998

[54] PROCESS FOR THE SYNTHESIS OF 2-HYDROXY-4-ALKYLOXY BENZOPHENONE

[75] Inventors: Marcello Notari, Parma; Franco Mizia, S. Donato Mil.se; Franco Rivetti, Milan, all of Italy

[73] Assignee: Enichem S.p.A., Milan, Italy

[21] Appl. No.: 974,924

[22] Filed: Nov. 20, 1997

[30] Foreign Application Priority Data

Dec. 5, 1996 [IT] Italy .................. MI96A2551

[51] Int. Cl.$^6$ .................. C07C 47/61
[52] U.S. Cl. .................. 568/315; 568/322
[58] Field of Search .................. 568/322; 566/315

[56] References Cited

U.S. PATENT DOCUMENTS

| 4,323,710 | 4/1982 | Wexler et al. |
| 5,629,453 | 5/1997 | Beau .................. 568/322 |

FOREIGN PATENT DOCUMENTS

| 0 371 255 | 6/1990 | European Pat. Off. |
| 06145091 | 5/1991 | Japan . |
| 1186818 | 4/1970 | United Kingdom . |

OTHER PUBLICATIONS

Patent Abstracts of Japan, vol. 18, No. 462 (C–1243), Aug. 29, 1994, JP 6–145091, May 24, 1994.

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

A process is described for the synthesis of 2-hydroxy-4-alkyloxy benzophenone by the selective alkylation of 2,4-dihydroxy benzophenone with a dialkyl carbonate, in liquid phase, in the presence of suitable catalysts, at a temperature ranging between 120° and 220° C. and at a total pressure ranging from 2 to 60 ate.

17 Claims, No Drawings

PROCESS FOR THE SYNTHESIS OF 2-HYDROXY-4-ALKYLOXY BENZOPHENONE

The present invention relates to a process for the synthesis of 2-hydroxy-4-alkyloxy benzophenone by the selective alkylation of 2,4-dihydroxy benzophenone with a dialkyl carbonate in liquid phase, in the presence of suitable catalysts.

Monoalkyloxy derivatives of 2,4-dihydroxy benzophenone are useful compounds which are applied as protection agents from UV radiation, mainly in the cosmetic field, in the textile industry and for the protection of the surface of polymers.

Alkylation processes of the potassium salt of 2,4-dihydroxy benzophenone to give 2-hydroxy-4-alkyloxy benzophenone, which make use of dialkylsulfate (EP-721.929) or alkyl halides (EP--32275) as alkylating agents, are known and industrially used.

These processes substantially have disadvantages deriving both from problems of toxicity of the alkylating reagents and from the disposal of waste products with a high saline content.

For example, dimethylsulfate is highly toxic by both inhalation and absorption, the $LD_{50}$ referring to rats is 440 mg/Kg, and in addition its use leads to the formation of potassium bisulfate in a stoichiometric quantity with the product in question. This makes a subsequent treatment of the waste water necessary, to avoid problems of pollution, with a consequent increase in the production costs.

To overcome these drawbacks, alkylation processes of phenols or their derivatives have been proposed in the art, which use dialkyl carbonates as alkylating agents. These reagents are not, in fact, very toxic and their use leads to the formation of waste products with a negligible saline content.

For example the patent U.S. Pat. No. 4,254,276 describes a process for the monomethylation of diphenol compounds, such as hydroquinone, with dimethylcarbonate in the presence of a catalytic system consisting of NaOH and KI.

Operating according to this process however, for high conversions of the starting diphenol compound, a low selectivity to the monomethylate product is obtained.

Patent application JP06145091 describes an alkylation process of diphenol compounds, such as hydroquinone, with dimethyl carbonate, in the presence of a basic catalyst, in a solvent selected from nitrogenated compounds, such as pyridine, DMF or quinoline. The use of this solvent makes it possible to operate at atmo- spheric pressure.

This process, however, has disadvantages deriving from the low conversions of the starting substrate. In fact, after 8 hours of reaction a conversion of 48% is obtained with a selectivity of 98% to the monomethylate product.

It has now been found that it is possible to obtain 2-hydroxy-4-alkyloxybenzophenone by the alkylation of 2,4-dihydroxybenzophenone with dialkylcarbonate with an unexpectedly high selectivity also with a high conversion of the starting diphenol compound, operating in the presence of suitable catalysts.

In accordance with this one object of the present invention relates to a process for the synthesis of 2-hydroxy-4-alkyloxybenzophenone having general formula

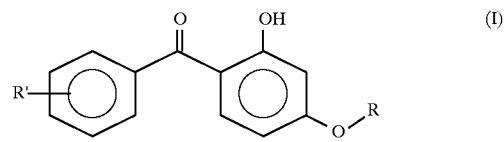

wherein: R' represents a hydrogen atom, an alkyl radical with from 1 to 20 carbon atoms or an arylalkyl radical with from 7 to 20 carbon atoms and R represents an alkyl radical with from 1 to 16 carbon atoms; an arylalkyl radical with from 7 to 20 carbon atoms, a cycloalkyl radical with from 5 to 10 carbon atoms, an alpha beta saturated alkene radical which contains from 3 to 6 carbon atoms;
by the selective alkylation of 2,4-dihydroxybenzophenone having general formula (II)

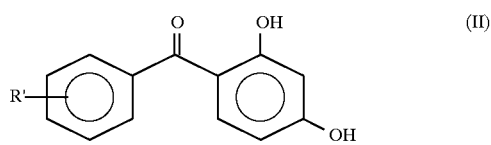

wherein R' has the same meaning defined above, with a dialkyl carbonate, in liquid phase, at a temperature of between 120° and 220° C. and at a total pressure ranging from 2 to 60 ate, in the presence of a catalyst selected from compounds of alkaline metals of a basic nature or from alkaline metal or alkyl halides.

In compounds having general formula (I), R' is preferably hydrogen and R is an alkyl radical preferably with 1 to 4 carbon atoms, an arylalkyl radical such as for example the benzyl radical, a cycloalkyl radical such as the cyclohexyl radical, an alpha beta saturated alkene radical such as the allyl radical.

Compounds having general formula (II) can be prepared according to one of the known methods, such as for example the process described in patent application EP-721929.

Dialkyl carbonates which can be used for the purposes of the present invention are compounds having general formula (III)

wherein R has the same meaning defined above.

Preferred dialkyl carbonates are dimethyl carbonate, diethyl carbonate and dipropyl carbonate. Dimethyl carbonate is particularly preferred.

The molar ratio between dialkylcarbonate and 2,4-dihydroxybenzophenone can vary within the range of 1.1:1 and 100:1, preferably within the range of 2:1 and 20:1.

Examples of catalysts which can be used in the process of the present invention include compounds of alkaline metals of a basic nature such as carbonates, oxides, hydroxides, alcoholates or halides of alkaline metals such as potassium iodide, or alkyl halides such as methyl iodide.

The preferred catalysts are potassium carbonate and potassium iodide.

The catalyst is used in quantities generally ranging between 0.005 and 0.2 moles, preferably between 0.01 and 0.1 moles, per mole of 2,4-dihydroxybenzophenone.

The alkylation reaction is usually carried out in liquid phase using the dialkylcarbonate itself as reaction solvent, or it can be carried out in the presence of an inert solvent.

Examples of solvents which can be used in the process of the present invention include alcohols, dimethylformamide, N-methylpyrrolidone, dimethylsulfoxide, acetonitrile, benzonitrile, dioxane, toluene, xylene and chlorinated solvents such as chlorobenzene.

When the solvent is an alcohol, it is preferable to use the alcohol corresponding to the radical present in the carbonate which is used.

The quantity of solvent, when used, is such as to give a weight ratio with respect to the 2,4-dihydroxy benzophenone ranging between 0.5:1 and 50:1, preferably between 1:1 and 20:1.

The alkylation reaction is carried out at temperatures of between 120° C. and 220° C., preferably between 140° C. and 180° C. and at total pressures of between 2 and 60 ate.

Total pressure refers to the pressure determined by the vapour pressure of the dialkyl carbonate, of the alcohol and, optionally, of the solvent used, at the reaction temperature (P1) and by the pressure of the carbon dioxide (P2) which is developed during the reaction.

It has now been found that if the catalyst is a halide of an alkaline metal, such as potassium iodide, the reaction can be carried out at the minimum operating pressure (P1) obtaining high yields of conversion and selectivity into the monoalkylated product.

When the catalyst is a compound of an alkaline metal of a basic nature, the partial pressure of the carbon dioxide must not be less than 2 ate. It has in fact been found that, when using these catalysts, with high conversion yields the selectivity is strongly influenced by the partial pressure of the $Co_2$.

The present invention is essentially based on the observation that in the process in question the pressure of the $Co_2$ which is developed in the reaction phase influences the quantity of by-products, in the sense that the latter tend to diminish with an increase in the pressure of the $CO_2$. Similar results are not obtained in the known processes.

The maximum value of the pressure of the $CO_2$ is not critical and is mainly linked to economic reasons. The pressures do not generally exceed 40 ate, the preferred values being within the range of 5 to 35 ate.

Operating within the range of preferred reaction conditions, the selectivity in the monoalkylated compound is generally higher than 93% for conversions of the starting diphenol compound within the range of 97% to 99%.

At the end of the reaction, the product is separated using the conventional techniques. For example the reaction mixture is subjected to distillation to remove the excess dialkyl carbonate, the co-produced alcohol and the inert solvent (when used) and subsequently the 2-hydroxy-4-alkyloxybenzophenone is recovered and purified by extraction and crystallization.

The process according to the present invention advantageously allows the monoalkylation of 2,4-dihydroxy benzophenone with high conversions and selectivity.

Some illustrative but non-limiting examples are provided for a better understanding of the present invention.

EXAMPLE 1

The reaction is carried out in a stainless-steel autoclave, with a capacity of 100 ml, equipped with a magnetic drag stirrer, manometer, thermocouple and plunged pipe equipped with a valve for the removal of samples.

15 g (0.07 moles) of 2,4-dihydroxy-benzophenone, 37.8 g (0.42 moles) of dimethylcarbonate and 0.2 g of potassium hydroxide are charged into the autoclave.

The stirring is activated and the autoclave is heated, by immersion in a thermostat-regulated oil bath, so as to have an internal temperature in the reactor of 160° C.

The reaction is carried out at the pressure which is spontaneously generated by the temperature and production of carbon dioxide.

After 12 hours of reaction at 160° C., the following results are obtained:

conversion of the 2,4-dihydroxy-benzophenone of 99.1% selectivity to 2-methoxy-4-hydroxy-benzophenone of 93.9%;

selectivity to 2,4-dimethoxy-benzophenone of 6%.

EXAMPLE 2

15 g (0.07 moles) of 2,4-dihydroxy-benzophenone, 37.8 g (0.42 moles) of dimethylcarbonate and 0.19 g of sodium methoxide are charged into a stainless-steel autoclave, equipped as described in example 1.

The stirring is activated and the reactor is heated with a thermostat-regulated oil bath, so as to have an internal temperature in the reactor of 160° C.

The reaction is carried out at the pressure which is spontaneously generated by the temperature and production of carbon dioxide.

After 8.5 hours of reaction at 160° C., the following results are obtained:

conversion of the 2,4-dihydroxy-benzophenone of 97.5% selectivity to 2-methoxy-4-hydroxy-benzophenone of 96%;

selectivity to 2,4-dimethoxy-benzophenone of 3.7%.

EXAMPLE 3

15 g (0.07 moles) of 2,4-dihydroxy-benzophenone, 37.8 g (0.42 moles) of dimethylcarbonate and 0.58 g of potassium iodide are charged into a stainless-steel autoclave, equipped as described in example 1.

The reaction is carried out at a temperature of 160° C. and the pressure which is spontaneously generated by the temperature and production of carbon dioxide.

After 7.5 hours of reaction at 160° C., the following results are obtained:

conversion of the 2,4-dihydroxy-benzophenone of 97.5% selectivity to 2-methoxy-4-hydroxy-benzophenone of 92%;

selectivity to 2,4-dimethoxy-benzophenone of 6%.

EXAMPLE 4

24.6 g (0.115 moles) of 2,4-dihydroxy-benzophenone, 41.4 g (0.46 moles) of dimethylcarbonate and 0.79 g of potassium carbonate are charged into a stainless-steel autoclave, equipped as described in example 1.

The reaction is carried out at a temperature of 160° C. and the pressure which is spontaneously generated by the temperature and production of carbon dioxide.

After 5 hours of reaction at 160° C., the total pressure inside the reactor is 34.5 ate., that of the $CO_2$ is about 27 ate. The following results are obtained:

conversion of the 2,4-dihydroxy-benzophenone of 96.8% selectivity to 2-methoxy-4-hydroxy-benzophenone of 96.8%;

selectivity to 2,4-dimethoxy-benzophenone of 3.1%.

After 6 hours of reaction, the total internal pressure is 35.5 ate., and the pressure of the $CO_2$ is about 28 ate. The following results are obtained:

conversion of the 2,4-dihydroxy-benzophenone of 99% selectivity to 2-methoxy-4-hydroxy-benzophenone of 95.6%;
selectivity to 2,4-dimethoxy-benzophenone of 4.3%.

EXAMPLE 5

The reaction is carried out in a stainless-steel autoclave, having a capacity of 250 ml, equipped with a magnetic drag stirrer, manometer, thermocouple and plunged pipe with a valve for the removal of samples.

The autoclave is connected to a steel water-cooled condenser, which has the function of condensing the vapours of dimethylcarbonate and methanol drawn in by the carbon dioxide which is flushed. from the system. The apparatus is connected at the head of the condenser to a control valve which allows the pressure in excess with respect to the desired value to be flushed away.

79.8 g (0.373 moles) of 2,4-dihydroxy-benzophenone, 134.2 g (1.49 moles) of dimethylcarbonate and 2.57 g of potassium carbonate are charged into the autoclave.

The stirring is activated and the autoclave is heated by immersion in a thermostat-regulated oil bath, so as to have an internal temperature in the reactor of 160° C.

The reaction is carried out at a pressure of 7.5 ate (the pressure of the $CO_2$ is about 0), maintained constant by a control valve which allows the carbon dioxide to be flushed, and test samples are taken at defined intervals of time. The results are shown in table 1.

TABLE 1

| time hours | Conversion % | Selectivity % | |
|---|---|---|---|
| | | Monomethylate | Bismethylate |
| 4.5 | 96.3% | 94% | 6% |
| 5.0 | 99.3% | 86.5% | 13.5% |
| 6.0 | 100% | 67% | 33% |

EXAMPLE 6

The same procedure is carried out as in example 5, but at a total pressure of 10 ate (pressure of the $CO_2$ about 2.5 ate). The results are shown in table 2.

TABLE 2

| time hours | Conversion % | Selectivity % | |
|---|---|---|---|
| | | Monomethylate | Bismethylate |
| 4.5 | 96.0% | 93.8% | 6.2% |
| 5.0 | 99.5% | 86.0% | 14.0% |
| 6.0 | 100% | 65.9% | 34% |

EXAMPLE 7

The reaction is carried out under the same conditions as example 5, but using a total pressure of 15 ate (pressure of the $CO_2$ about 7.5 ate). The results are shown in table 3.

TABLE 3

| time hours | Conversion % | Selectivity % | |
|---|---|---|---|
| | | Monomethylate | Bismethylate |
| 4.5 | 97.7% | 95% | 5.0% |
| 5.0 | 99.4% | 93.0% | 7.0% |
| 6.0 | 100% | 88.4% | 11.6% |

EXAMPLE 8

The same procedure is carried out as in example 5, but using 3.09 g of potassium iodide as catalyst.
The results are shown in table 4.

TABLE 4

| time hours | Conversion % | Selectivity % | |
|---|---|---|---|
| | | Monomethylate | Bismethylate |
| 7.0 | 97.7% | 94.3% | 5.3% |
| 7.5 | 99.4% | 92.3% | 6.7% |
| 8.5 | 99.9% | 85.5% | 13.2% |

We claim:
1. A process for the preparation of 2-hydroxy-4-alkyloxybenzophenones having formula (I)

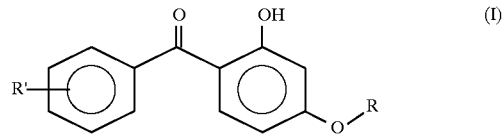

wherein
R' represents a hydrogen atom, an alkyl radical with from 1 to 20 carbon atoms, an arylalkyl radical with from 7 to 20 carbon atoms, and
R represents an alkyl radical with from 1 to 16 carbon atoms, an arylalkyl radical with from 7 to 20 carbon atoms, a cycloalkyl radical with from 5 to 10 carbon atoms or an alpha beta unsaturated alkene radical which contains from 3 to 6 carbon atoms;
by the selective alkylation of a 2,4-dihydroxy-benzophenone having formula (II)

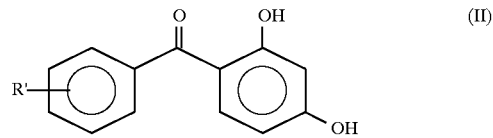

wherein
R' has the same meaning defined above,
with a dialkyl carbonate, in a liquid phase, at a temperature of between 120° and 220° C. and at a total pressure ranging from 2 to 60 ate, in the presence of a catalyst selected from the group consisting of compounds of alkaline metals of a basic nature, halides of alkaline metals, and alkyl halides,
with the proviso that when the catalyst is a compound of an alkaline metal of a basic nature, the alkylation reaction is carried out at a partial pressure of the carbon dioxide which is developed under the reaction conditions of not less than 2 ate.
2. The process according to claim 1, wherein R is an alkyl radical with from 1 to 4 carbon atoms, an arylalkyl radical, a cycloalkyl radical, an alpha beta unsaturated alkene radical.

3. The process according to claim 1, wherein the catalyst is selected from the group consisting of potassium carbonate and potassium iodide.

4. The process according to claim 1, wherein the dialkylcarbonate is selected from compounds having general formula (III)

wherein R has the meaning as defined in claim 1.

5. The process according to claim 4, wherein the dialkyl carbonate is selected from the group consisting of dimethyl carbonate, diethyl carbonate and dipropyl carbonate.

6. The process according to claim 5, wherein the dialkyl carbonate is dimethyl carbonate.

7. The process according to claim 1, wherein the molar ratio between the dialkyl carbonate and the 2,4-dihydroxy-benzophenone is between 1.1:1 and 100:1.

8. The process according to claim 7, wherein the molar ratio between the dialkyl carbonate and the 2,4-dihydroxy-benzophenone is between 2:1 and 20:1.

9. The process according to claim 1, wherein the alkylation reaction is carried out in liquid phase in an inert solvent selected from alcohols, dimethylformamide, N-methylpyrrolidone, dimethylsulfoxide, acetonitrile, benzonitrile, dioxane, toluene, xylene and chlorinated solvents.

10. The process according to claim 9, wherein the weight ratio of the solvent to the 2,4-dihydroxybenzophenone is 0.5:1 to 50:1.

11. The process according to claim 10, wherein the weight ratio of the solvent to the 2,4-dihydroxybenzophenone is 1:1 to 20:1.

12. The process according to claim 1, wherein the catalyst is used in quantities of between 0.005 and 0.2 moles, per mole of 2,4-dihydroxy-benzophenone.

13. The process according to claim 12, wherein the catalyst is used in quantities of between 0.01 and 0.1 moles, per mole of 2,4-dihydroxy-benzophenone.

14. The process according to claim 1, wherein the alkylation reaction is carried out at temperatures of between 140° C. and 180° C.

15. The process according to claim 1, wherein, when the catalyst is a compound of an alkaline metal of a basic nature, the partial pressure of the carbon dioxide is less than 40 ate.

16. The process according to claim 15, wherein the partial pressure of the carbon dioxide is between 5 and 35 ate.

17. The process according to claim 1, wherein the selectivity for production of the 2-hydroxy-4-alkyloxybenzophenone having formula (I) is higher than 93% and the conversion of the 2,4-dihydroxy-benzophenone having formula (II) is 97% to 99%.

* * * * *